(12) United States Patent
Pinault et al.

(10) Patent No.: US 8,740,880 B2
(45) Date of Patent: Jun. 3, 2014

(54) DEVICE FOR POSITIONING A PATIENT WITH RESPECT TO A RADIATION

(75) Inventors: Samuel Pinault, Issy les Moulineaux (FR); Régis Ferrand, Versailles (FR); Jérôme Chemouny, Villeparisis (FR)

(73) Assignee: Bureau Francais d'Ingenierie, Villebeon (FR)

(*) Notice: Subject to any disclaimer, the term of this patent is extended or adjusted under 35 U.S.C. 154(b) by 1175 days.

(21) Appl. No.: 12/665,276

(22) PCT Filed: Oct. 30, 2009

(86) PCT No.: PCT/FR2009/052103
§ 371 (c)(1),
(2), (4) Date: Dec. 17, 2009

(87) PCT Pub. No.: WO2010/049660
PCT Pub. Date: May 6, 2010

(65) Prior Publication Data
US 2011/0066278 A1 Mar. 17, 2011

(30) Foreign Application Priority Data
Oct. 31, 2008 (FR) ..................................... 08 57442

(51) Int. Cl.
*A61B 17/00* (2006.01)
(52) U.S. Cl.
USPC ..................... 606/1; 606/130; 700/245; 901/6
(58) Field of Classification Search
USPC .................. 606/1, 130; 5/600, 601, 607–612, 5/616–619; 378/65, 193, 195–198; 414/754, 757–760; 700/90, 213, 245; 901/2, 6, 8–11, 14–18
See application file for complete search history.

(56) References Cited

U.S. PATENT DOCUMENTS

| 6,094,760 | A | 8/2000 | Nonaka et al. |
| 7,520,006 | B2* | 4/2009 | Menkedick et al. ............ 5/618 |
| 2003/0048875 | A1 | 3/2003 | Mihara et al. |
| 2004/0184579 | A1* | 9/2004 | Mihara et al. .................. 378/65 |
| 2005/0234327 | A1 | 10/2005 | Saracen et al. |
| 2009/0044334 | A1* | 2/2009 | Parsell et al. ..................... 5/424 |
| 2011/0023285 | A1* | 2/2011 | Cooper ........................... 29/428 |
| 2011/0118748 | A1* | 5/2011 | Itkowitz ........................ 606/130 |

FOREIGN PATENT DOCUMENTS

| WO | WO 2007/017211 | A2 | 2/2007 |
| WO | WO 2007/112602 | A1 | 10/2007 |
| WO | WO 2008/005129 | A2 | 1/2008 |
| WO | WO 2008/110170 | A1 | 9/2008 |

OTHER PUBLICATIONS

Meggiolaro et al., "Geometric and Elastic Error Calibration of a High Accuracy Patient Positioning System", Mechanism and Machine Theory 40 (2005) pp. 415-427.

* cited by examiner

*Primary Examiner* — Ahmed Farah
(74) *Attorney, Agent, or Firm* — Greer, Burns & Crain, Ltd.

(57) ABSTRACT

A device is provided for positioning a patient with respect to a radiation, the device being a polyarticulated robot including: —at least one linear horizontal displacement rail, —a connecting part capable of carrying out translations with respect to the linear rail and pivoting about an axis of rotation vertical to that linear rail, and —a robotic arm connected to the connecting part, the robotic arm including a wrist with concurrent axes of rotation connected to a patient support.

17 Claims, 6 Drawing Sheets

DEVICE FOR POSITIONING A PATIENT WITH RESPECT TO A RADIATION

Figure 1:
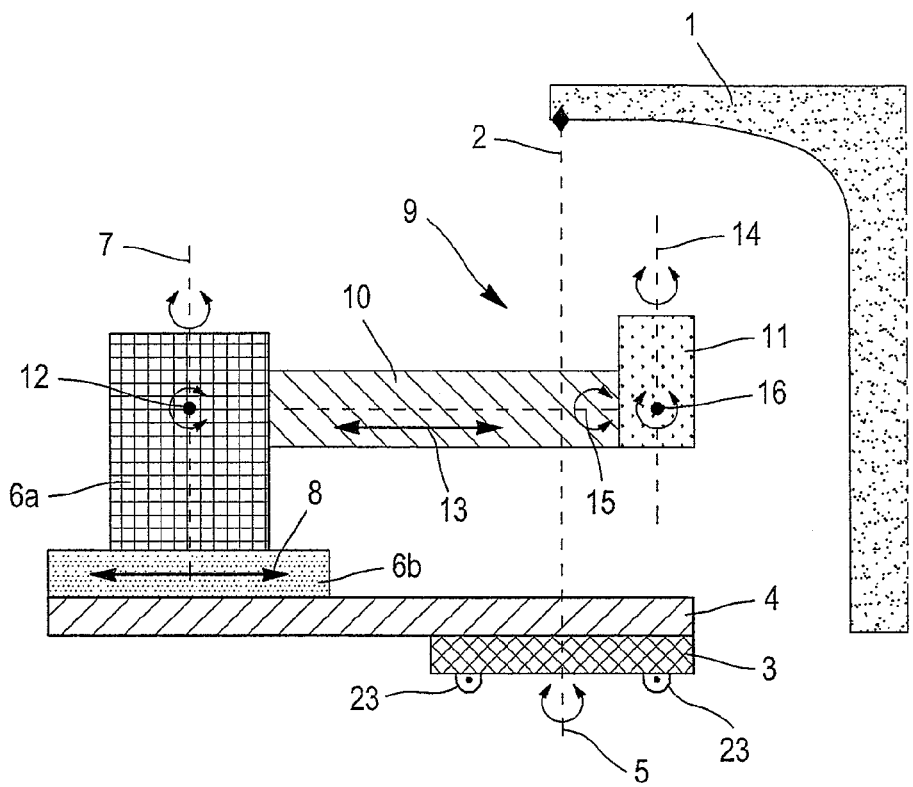

The present invention relates to a device for positioning a patient with respect to an external radiotherapy beam. It has a particularly advantageous application in the field of radiotherapy where irradiation beams are used for treatments requiring very high precision, for example for melanoma of the choroid or for certain intra-cranial tumours. When a tumour is in particular located at the base of the skull of a patient, the purpose of the radiotherapy is to irradiate the malignant areas whilst avoiding touching critical organs, such as the optic nerves, the brain stem, the inner ear or the spinal cord which are nearby. It is therefore of prime importance to position the patient correctly with respect to the radiation intended to irradiate a tumour. In radiotherapy, the patient is generally placed on a table or a chair and then positioned using electromechanical equipment.

However, the present invention has a wider scope since it can be applied to other fields requiring the accurate positioning of a patient or any other object. The present invention can for example be applied to medical applications of any kind, requiring the precise and rapid positioning of a patient with respect to a given frame of reference.

In the prior art, document US 2005/0234327 describes a device for positioning a patient comprising a table for carrying the patient, having a robotic arm with SCARA morphology provided with a prismatic link allowing displacements along a vertical axis, two consecutive vertical rotoidal links and a robotic wrist with concurrent axes. The defect of such a device is the exact modelling of the mechanical elasticity when the robotic arm is extended to the maximum with a patient placed above. A sophisticated software correction table system must be installed in order to obtain the accuracies required for a medical application. Moreover, the vertical translation axis undergoes considerable stresses, which can limit the lifetime of the link components and increase the size. Moreover, this translation axis requires the installation of the device in a pit more than one meter deep.

Moreover, the document "Geometric and elastic error calibration of a high accuracy patient positionning system", Marco A. Meggiolaro and al., Mechanism and Machine Theory 40 (2005) 415-427, 12 Sep. 2004, describes a method of compensating for the deformations of another electromechanical system for the positioning of a patient. The robotic model described is provided with three linear shafts for the vertical, lateral and longitudinal translations. It furthermore has three non-concurrent axes of rotation under the fixing interface with the treatment table. This positioning device which has six degrees of freedom provides limited possibilities of pitch and roll (±3 degrees). Moreover, the control of this device does not allow the carrying out of complicated movements such as rotations about a virtual reference point remote from the wrist, related to the tumour, as offered by any robotic system. This equipment has the same defects as the preceding system, namely mechanical elasticity and the requirement for a deep pit in the treatment room.

Document WO2007/017211 describes a positioning device using an industrial robot having a plurality of axes of rotation able to position a patient suitably. However, such a device is very bulky and requires a pit of large dimensions able to house the bottom part of the positioning device. The installation of such a device in a treatment room is therefore very costly and imposes many constraints.

A purpose of the present invention is to overcome the drawbacks of the prior art by proposing a new positioning device which is compact and very rigid, intrinsically having high precision and not needing a deep pit.

A subject of the invention is the development of a positioning robot which is simple to install.

Finally, a purpose of the invention is to propose a high-performance control of the positioning robot in order to give the best possible guarantee of the safety of the patient and of the attending personnel during the movements.

At least one of the abovementioned purposes is achieved with a device for positioning a patient with respect to a radiation; this device is a polyarticulated robot comprising:
  at least one linear horizontal displacement rail,
  a connecting part capable of carrying out translations with respect to the linear rail and of pivoting about an axis of rotation vertical with respect to that linear rail, and
  a robotic arm connected to the connecting part, this robotic arm comprising a wrist with concurrent axes of rotation connected to a patient support.

The invention advantageously constitutes a positioning robot which is very compact but capable of manoeuvring with very high precision in an extensive space. The overall dimensions are greatly reduced in comparison with the devices of the prior art. In fact, the geometry described differs from the conventional morphologies by the order and the angles used for the arrangement of the mechanical segments constituting the robot. The "SCARA", polyarticulated or hexapodic concepts previously described have the major drawback of requiring a deep pit in the ground.

Moreover, the present invention is innovative in terms of overall dimensions and of compactness when in the folded position in the room. In order to make the working space of such a system optimal, it must be centred on a plane whose height above the floor can vary from one meter and twenty centimeters to one meter and fifty centimeters. This constraint is inherent in the principle of radiotherapy beam treatment.

The subject of the present invention is even more noteworthy in that it constitutes a hybrid positioning robot, the link between the shoulder and the elbow of the polyarticulated morphology known as "serial" (robot with movements of the human arm type) is advantageously replaced by the coupling of the linear axis on the floor and of the previously described connecting part on a vertical pivot. These changes overcome the two constraints of mobility (translation axis) and compactness (connecting part). The robot is compact because the rail makes it possible to move the robotic arm assembly (from the connecting part to the patient support) in translation up to the location provided for by the treatment schedule. The robotic arm, with its multiple degrees of freedom, can then carry out movements of small amplitude but requiring high precision in order to optimize the position of the target to be treated in the treatment frame of reference.

This compact positioning robot with six degrees of freedom makes it possible to limit the depth of the pit and is capable of transporting heavy loads of at least 250 kg with the overall dimensions of a standard radiotherapy table. With such a linear rail according to the invention, it is possible to provide a short robotic arm, of approximately 1 m 30. This positioning robot has increased stiffness and compactness in comparison with a system of the prior art insofar as this robot does not have an offset axis, far from the base.

The invention, because of the compactness of its morphology, has a centre of gravity fairly close to its base in order to limit the cantilever effect observed in the devices of the prior art. All of the weight of the positioning robot is therefore distributed over the ground, which improves the stability and the rigidity of the device.

The positioning robot according to the invention makes it possible to optimize and adapt the working space to a given application. In fact, the size of the linear rail can vary according to the available space and of the desired optional functions. It is thus envisaged to increase the length of the axis in order to carry out a pre-positioning of the patient using an imaging scanner on one side of the room and then sending the patient directly into the treatment position under the radiotherapy device by a pure translation of the base of the robot. This functionality would advantageously replace the current procedures which are tedious and ill suited to certain treatments in paediatrics in particular.

According to another way of assembling the axes of the robot, the linear rail can be fixed to a pivoting part of a base, the pivot axis of this pivoting part being vertical. In the case of such an assembly, the system can be installed in a shallow pit (having a maximum depth of the order of 300 mm). By the addition of this new axis, the robot comprises seven axes combining six rotations and a translation, giving a maximum mobility of six degrees of freedom. This addition makes the architecture redundant and makes it possible to reach positions of difficult access in a congested environment such as a treatment room.

In practice, in order to ensure good precision, provision is made for the pivoting part to pivot with respect to a fixed part of the base by means of a ball bearing. The fixed part of the base can comprise mounts made of aluminium profile fixed to the ground in a small pit for example. The assembly thus produced makes it possible to carry out a 360° rotation of the assembly comprised of linear rail and robotic arm. The working envelope of such equipment corresponds to a half-sphere with no dead zone.

Preferably, the axis of vertical rotation of the linear rail with respect to the base is merged with the axis of or plumb of said radiation. Thus, when a target, for example in the head of a patient, is appropriately positioned with respect to the radiation, a pure rotation of the axis on the ground suffices to rotate the patient, change the angle of incidence of the radiation, whilst keeping the target in the axis. This makes it possible to envisage a dynamic treatment of the patient by combining the displacement of the robot with the form of the multi-slits collimator shaping the beam.

Advantageously, the robotic arm comprises a sliding forearm. The advantage is to have a calibration volume connected to the terminal of the robot (in which the robot is very accurate) which follows the linear axis. This volume moves along a very precise axis (linear axis precision <0.1 mm) and it is possible to have a precision volume continuously following the zone to be treated. The terminal, sometimes called the effector, corresponds to the end of the robot (positioning device). It is generally an attachment plate between the robot and the patient support.

With a linear rail according to the invention, it is then possible to simplify the calibration of the positioning device. In fact, a limited number of measurement points can be produced, for example eight points at the corners of a cubic volume. Then, within this volume, a certain number of Cartesian positions are calculated maximizing large articular variations for each displacement. The robot will have a very high precision in this volume, connected to its terminal, which will move very accurately along the linear axis.

The robotic arm can be connected to the connecting part pivoting about a horizontal axis of rotation.

According to another variant of the invention, the robotic arm is connected to the connecting part in a pivoting manner about an axis of rotation which is inclined with respect to the horizontal by an angle of between 0° and 90°. Preferably, the axis of rotation of the robotic arm with respect to the connecting part is inclined with respect to the horizontal by an angle of between 45 and 60 degrees. This inclination is in particular useful for the reversal of the arm (passage of the arm from the front of the robot towards the rear) in a confined space with a lower under-ceiling height.

Moreover, the connecting part can be connected, pivoting about a vertical axis, to a seat which is connected in a sliding manner to said at least one linear rail.

The wrist is connected to the patient support by means of a standard electro-pneumatic tool changer.

According to an advantageous feature of the invention, the connecting part moves by rolling on the linear rail designed as a U-section steel profile.

Advantageously, the device according to the invention is designed in such away as to limit handling during the installation in the treatment room, by means of the addition of detachable or retractable wheels which support the device during an installation. These wheels can be fixed to the base of the chassis of the device. This facilitates the handling of the device and the easy replacement of a positioning device in an existing room.

According to an advantageous feature of the invention, the device comprises a mobile platform constituted by two half-platforms connected to the connecting part and arranged on either side of this connecting part in order to constantly cover the linear rail when the connecting part moves; each half-platform is constituted by several slats chain-linked to each other by hinges, such that when a half-platform is in the folded position, at least some of the slats of this half-platform are concertinaed under a horizontal plane which contains this half-platform in the unfolded position.

Preferably, the platform slides on two sets of secondary rails:
  a first set of inner secondary rails upon which slides half of the hinges, these two inner secondary rails being parallel and separated from each other; these two inner secondary rails having an upper linear part, a bend point and a lower linear part;
  a second set constituted by two outer secondary rails upon which slides the other half of the hinges, these two outer secondary rails being parallel and separated by a distance greater than the distance separating the two inner secondary rails; these two outer secondary rails being linear in a horizontal plane substantially at the same height as the upper linear part of the inner secondary rails;
and, for two successive hinges, one is borne by the first set of secondary rails, the other being borne by the second set of secondary rails.

Advantageously, each half-platform has, in the unfolded position, a flat part close to the connecting part and, in the folded position, a part concertinaed between the lower linear part of the inner secondary rails and the outer secondary rails.

According to an advantageous variant of the invention, the platform is fixed. In this case, the linear rail is constituted by a plurality of modular elements fixed to the floor and connected to each other. These modular elements can for example have a length of 1 m and make it possible to adapt the travel of the robot to a given application such as the placing of a scanner on one side of the room and of a treatment accelerator on another side.

According to another aspect of the invention, a positioning system is proposed comprising a positioning device as defined previously, a processing unit integrating supervision software, a series of patient resetting sensors and in particular a series of safety sensors.

Displacements are verified by the installation of sensors and software. The sensors used are in part sophisticated sensors such as an infrared stereovision sensor capable of following the displacement of targets of known geometry, X-ray sensors, industrial cameras and a force sensor on the terminal member of the robot. All the data collected by these sensors meet in a common processing centre called a supervisor. The supervisor knows the current state of the environment of the robot and can compare it with the theoretical configuration of the room for the required task. This comparison is accompanied by a possible modification of the trajectory in the case of avoiding obstacles, a reduction in speed on approaching a potentially dangerous zone or a warning to the operator in the case of a problem. Each change with respect to the original scenario is signalled to the operator in the supervision interface. Safety is enhanced by the addition of a layer of low-level sensors: resolvers, accelerometers, pulse counters on each axis, inclinometers, anti-collision strips, whose function is to cut off the robot's power in the event of overshooting the limits imposed by the regulations governing the installation of electro-mechanical systems in a medical environment.

According to the invention, the processing unit can comprise a 3D display module provided with:
  a virtual 3D modelling of the treatment room in which the positioning device is located;
  a virtual 3D modelling of the positioning device; this modelling being parameterized in order to represent the real-time positioning of the positioning device on the basis of sensors, and to define a virtual envelope around at least one element of the positioning device in order to generate an alarm signal when the virtual envelope collides with a virtual representation of an element of the treatment room.

The processing unit can be parameterized in order to initiate, in response to the alarm signal, an anti-collision process consisting in the stopping of the positioning device or the reorientation of the movement of the positioning device.

With the system according to the invention, a remote control of the positioning robot improves the safety of the displacements thanks to the optimization of the chosen trajectories and to the facilitated interpretation of the commands to be sent. The 3D display module is in particular useful for the visualization of the scene and of the movement of the robot. On the basis of measurements by the sensors (position of the robot) and the precise simulation of each part of the system (treatment accessory, table or chair), it is possible to anticipate and avoid collisions. This functionality is advantageously based on virtual envelopes around each of the elements (fixed or mobile) present in the treatment room. This embodiment constitutes an anti-collision system allowing the movement of the robot in the treatment room without risk of collision.

According to another advantageous feature, the device according to the invention comprises at least one force sensor fixed to the wrist, preferably to the terminal of the positioning device, and connected to a processing unit controlling said positioning device so as to carry out a co-manipulation accompanying any force detected by said at least one force sensor. More precisely, the force sensor can comprise six strain gauges. The detected forces are transmitted to the processing unit (a computer for example) which processes them and sends to the robot the command for displacement in the direction of the force. This control loop allows a user to manipulate the tool without any mass constraint. The inertias and the weights are compensated for by the robot. The possibilities of movement are those of the robot, i.e. the six degrees of freedom, three translations and three rotations.

This embodiment allows a manual manipulation of the robot. The objective is in particular to move a patient placed on the support by co-manipulation in order to align him or her intuitively in front of an imaging or treatment apparatus using standard laser systems. This manual patient placement operation makes it possible to reduce positioning times. It is a pre-positioning which can also be advantageously used for an intuitive emergency extraction of the patient in the case of discomfort. This method is intuitive because the force that a user applies to the robot is relayed by a slaved displacement of the positioning device which controls an electromechanical system.

The force sensor can also be used to measure the supported load. This measurement is used to adjust the enslavement parameters for the co-manipulation, and also to gain an idea of the deformations undergone by the robot and thus to compensate for them. This direct measurement by the sensor is automated and is consequently completely transparent to the user.

The force sensor can also be used to detect collisions with moving objects. During a displacement of the robot following a predefined or dynamic trajectory, or during any other manoeuvre, the tool can collide with other elements of the environment (human, trolley, etc.). These collisions give rise to unexpected forces on the sensor and it is therefore possible to carry out an emergency stop on the robot in order to prevent damaging one or other of the colliding objects.

Figure 2:
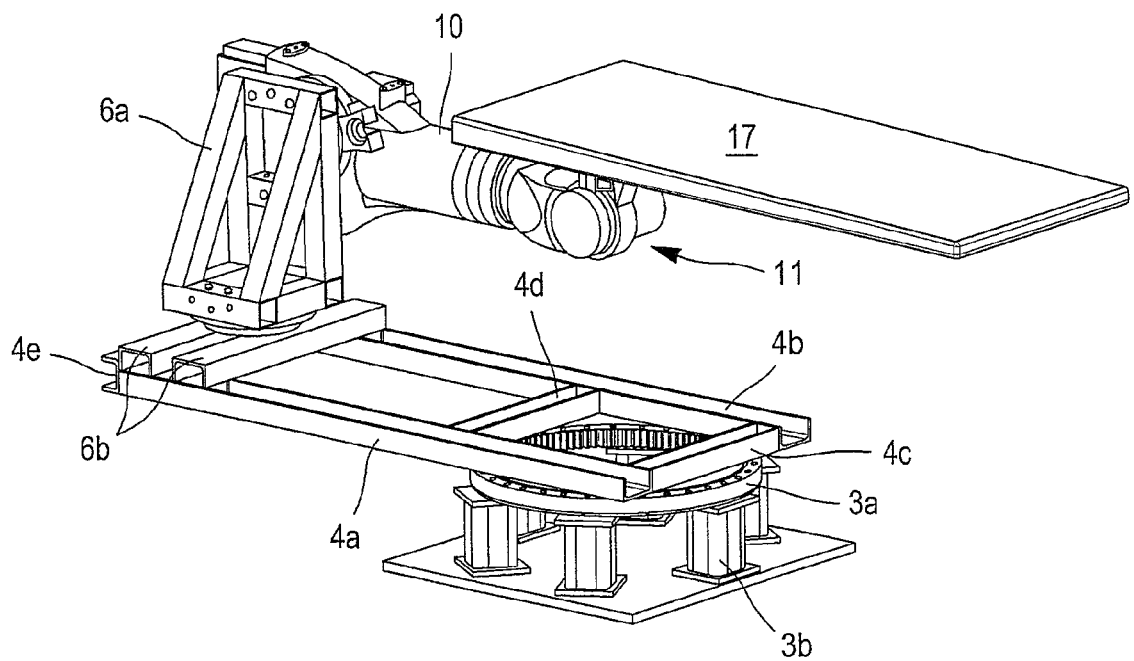
Figure 3:
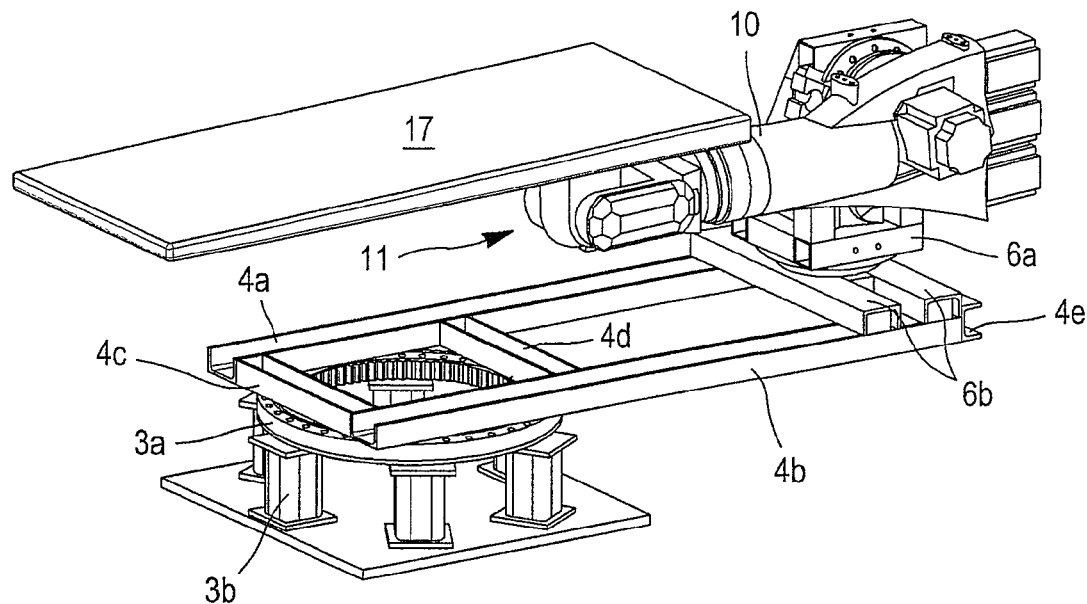
Figure 4:
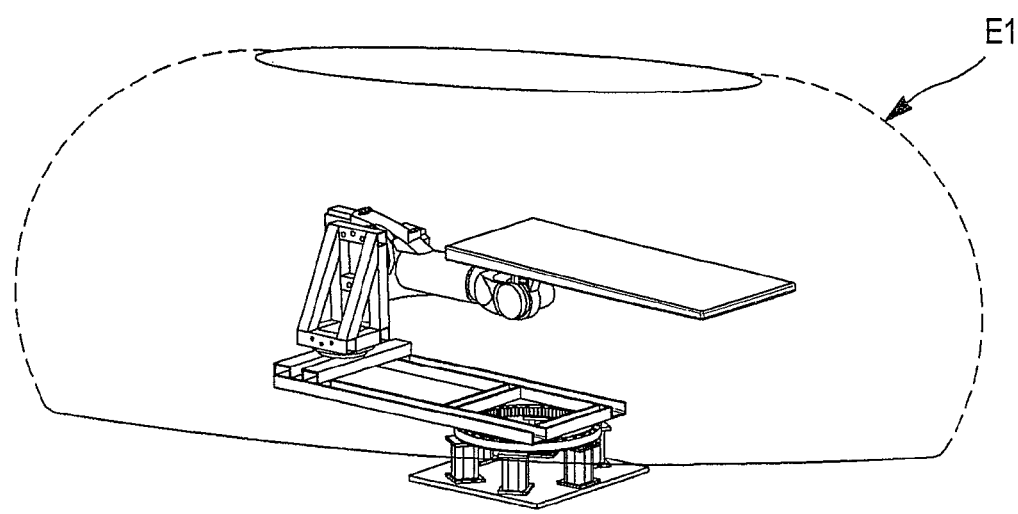
Figure 5:
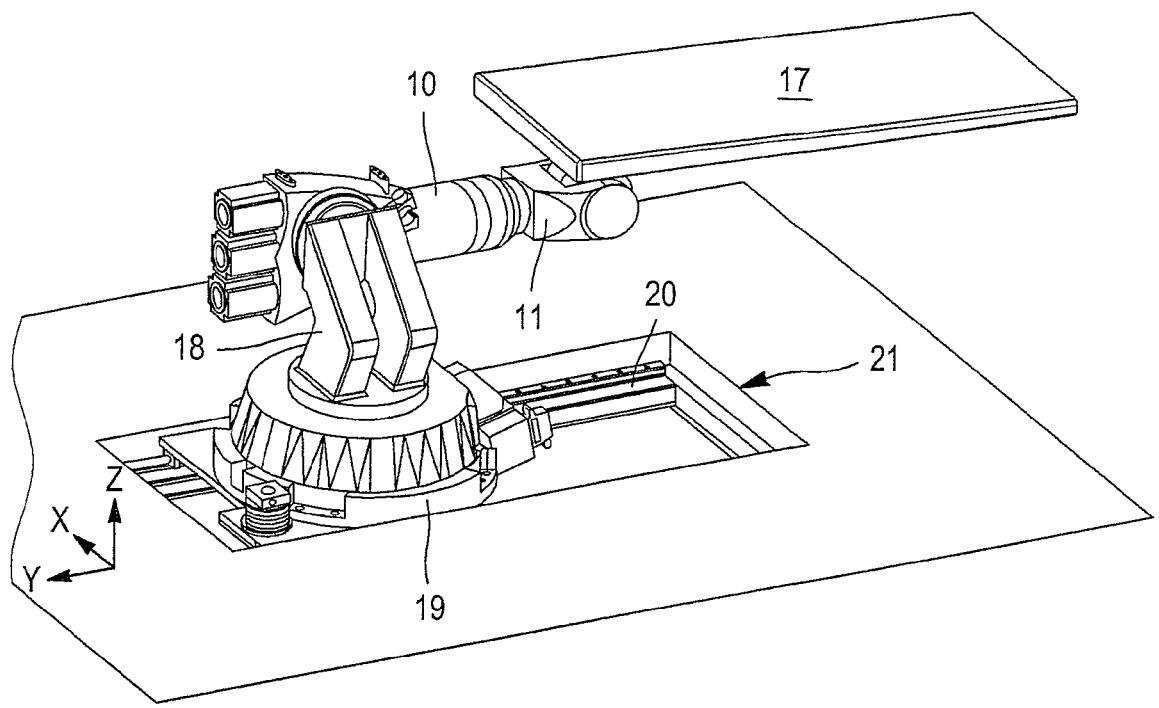
Figure 6:
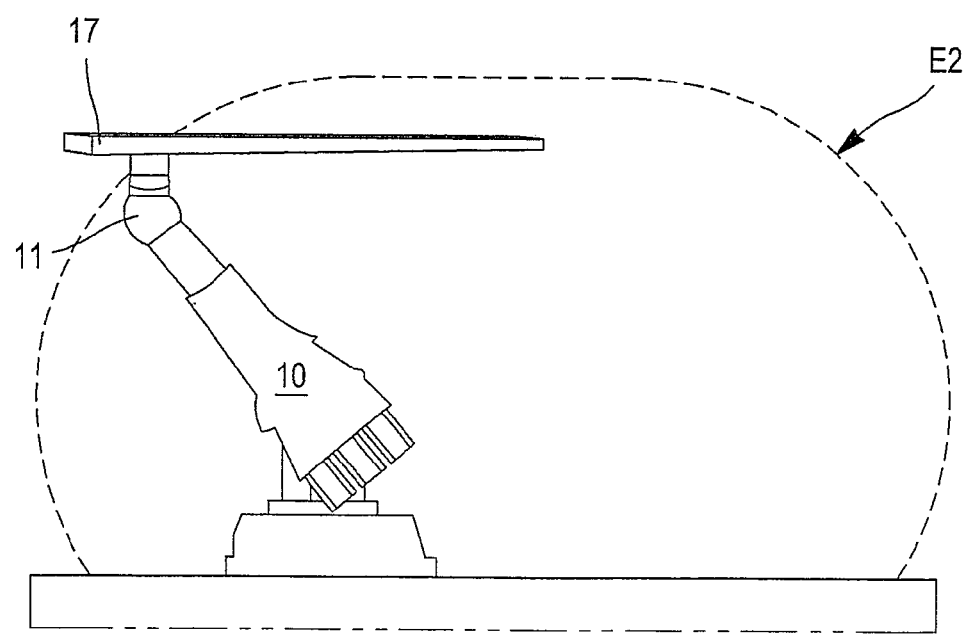
Figure 7:
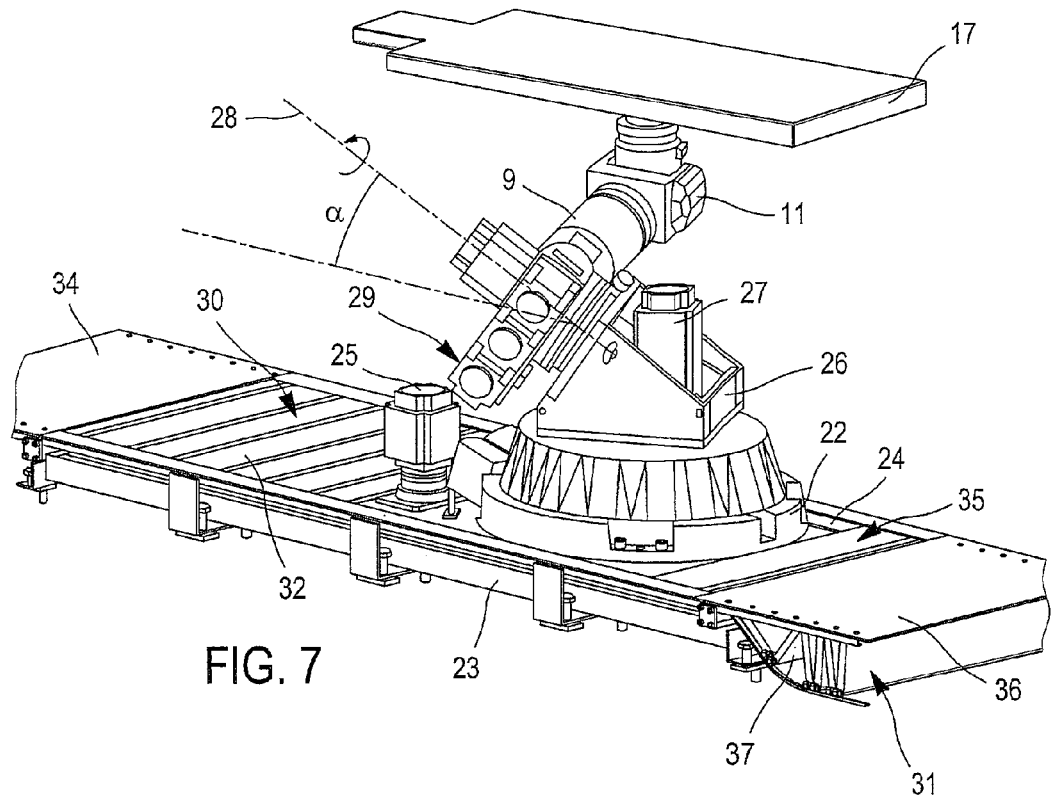
Figure 8:
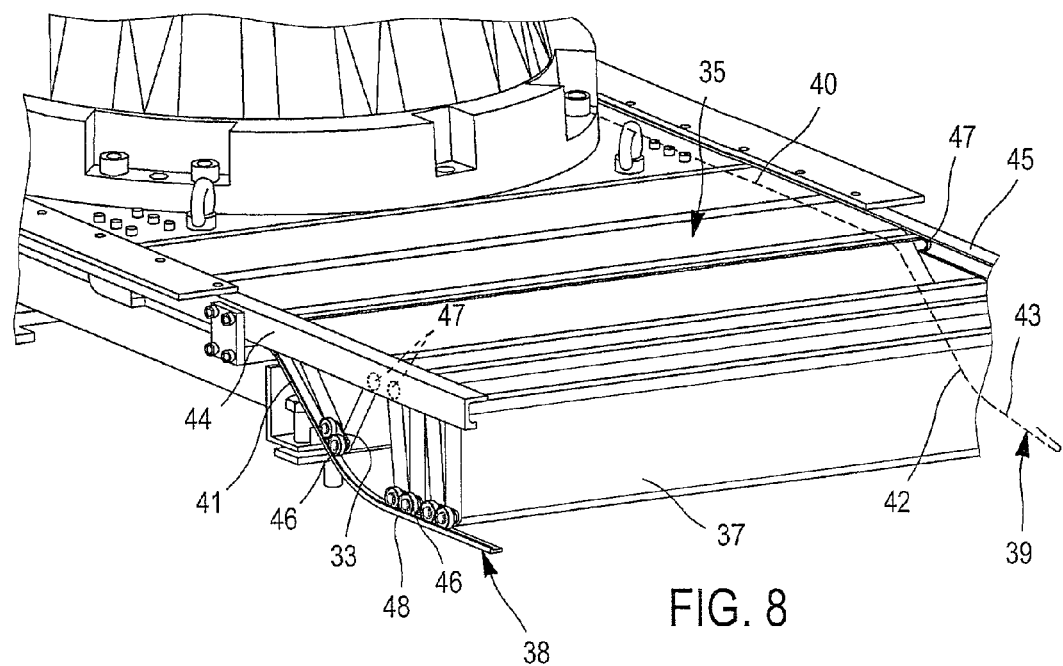
Figure 9:
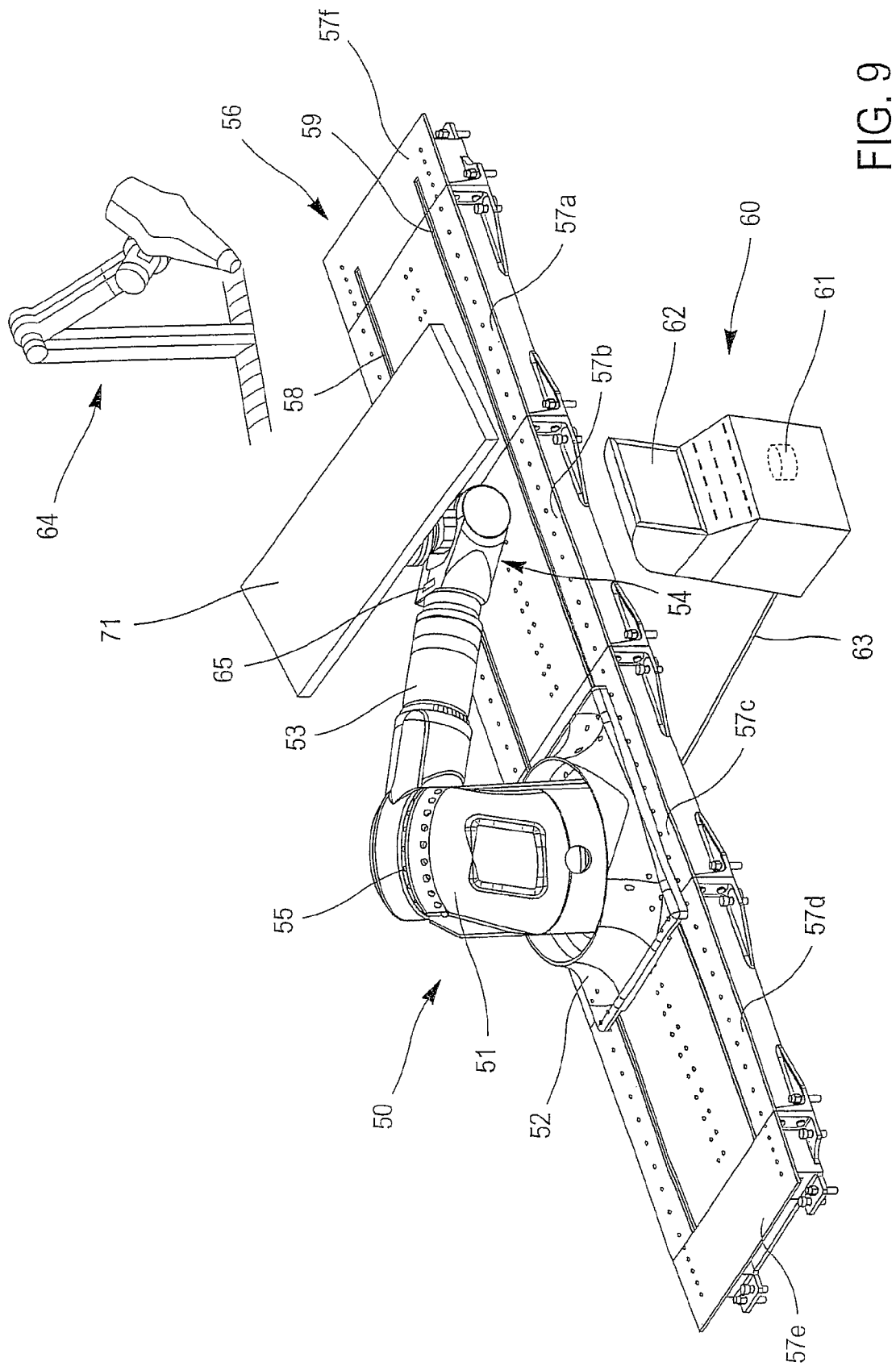
Figure 10:
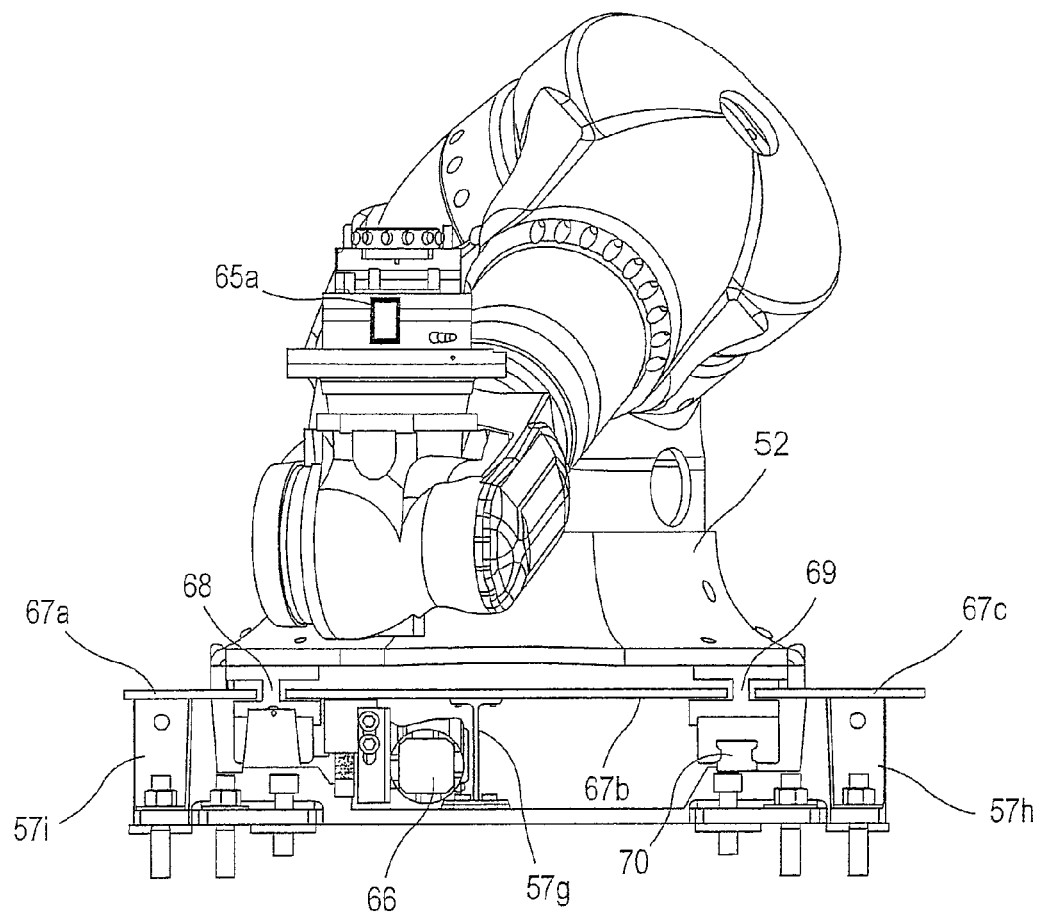
Figure 11:
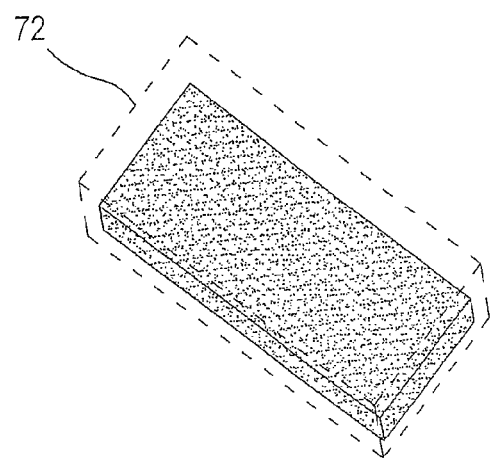

Other advantages and features of the invention will become apparent on examination of the detailed description of an embodiment, which is in no way limitative, and the attached drawings in which:

FIG. 1 is a schematic view illustrating the kinematic principle of a positioning robot according to the invention, FIG. 2 is a first schematic side view of the positioning device according to the invention, FIG. 3 is a second schematic side view of the positioning device according to the invention, FIG. 4 is a schematic view showing a working space in which the positioning robot according to the invention can move, FIG. 5 is a schematic view of a positioning robot according to the invention for which the linear rail is fixed to the floor, FIG. 6 is a schematic view of the positioning robot according to the invention in a deployed position, FIGS. 7 and 8 are schematic views illustrating an embodiment in which the platform on the linear rail is mobile, FIG. 9 is a schematic view of an embodiment in which the platform is fixed and composed of modular elements;

FIG. 10 is a schematic side view of the positioning robot of the FIG. 9 without the patient support; and FIG. 11 is a virtual representation of a patient support of the positioning robot of FIG. 9.

A positioning robot according to the invention is generally intended for positioning a patient with respect to an ionizing radiation during external radiotherapy. Such a positioning robot is placed in a room having dimensions suitable for such therapeutic treatments. This room is equipped with a particle accelerator which is capable of generating radiation focussed on the tumour to be treated in the body of the patient. It will easily be understood that the positioning of the patient must be as accurate as possible and stable throughout the treatment.

A positioning robot is an articulated arm which carries a support table or a support chair or any other support means upon which a patient is placing. The articulations of the positioning robot are controlled by a processing unit and are able to position the patient's tumour at any point within a three-dimensional working space.

FIG. 1 is a diagrammatic view illustrating the kinematic principle of a positioning robot according to the invention. A particle generator 1 is provided for generating radiation downwards along a vertical axis 2.

The positioning robot comprises a base 3 on which a linear rail 4 can pivot about a vertical axis of rotation 5. Advantageously, this vertical axis of rotation 5 can be merged with the axis 2 of the radiation. The positioning robot also comprises a connecting part 6a fixed on a seat 6b in a pivoting manner about a vertical axis of rotation 7. The seat 6b can move linearly, by translation, on the linear rail 4 along a horizontal axis of translation 8. The connecting part 6a carries a robotic arm 9 comprising a forearm 10 and a wrist 11. The forearm 10 is fixed to the connecting part 6a in a pivoting manner about a horizontal axis of rotation 12. Preferably, the forearm 10 is of the sliding type such that it can elongate linearly along a linear axis 13. The end of the forearm 10 most distant from the connecting part 6a carries the wrist 11 having three degrees of freedom about three orthogonal and concurrent axes of rotation 14, 15 and 16. This wrist 11 is fixed to the sliding part of the forearm 10. The support table (not shown), intended to receive the patient, is generally fixed horizontally on the wrist 11.

In a conventional manner, the positioning robot according to the invention is connected to a processing unit (not shown) capable of managing the articulations of this positioning robot in order to place the tumour of a patient in a predetermined position. This processing unit gathers in real time the articular positions of each of the axes by means of encoders fixed to the motors. Then, on the basis of theoretical parameters resulting from the calibration of the robot, the processing unit is able to provide the user with a Cartesian position of the reference frame of the tumour with respect to the virtual treatment reference frame. Thus, the user can easily interpret this position and verify that it conforms to the prescription. In the same way, the user can validate a correction to be applied to the reference frame of the tumour in the treatment reference frame as proposed by the system used for adjusting the patient (scanner, X-rays, infrared). Then, this command is analyzed and transcribed into an articular command to the robot.

The invention is moreover provided with advanced 3D display software, based on a theoretical model of the scene and on the information gathered by the various sensors present. This fine modelling of the positioning procedure makes it possible to consider eventually shifting the controls outside of the treatment room. This shift will advantageously make it possible to displace the positioning device remotely and thus reduce the time wasted, by the operator, in entering the room again in order to change the treatment incidence of the patient.

FIGS. 2 and 3 show an embodiment example of the positioning robot according to the invention. The base 3 is constituted by a ring 3a, a pivoting part, mounted on blocks 3b made from aluminium profile firmly fixed to the floor.

The linear rail 4 is a frame formed by two straight rails, of parallel runners with bearings 4a and 4b, preferably made of U-section steel profile. These two rails 4a and 4b are connected together by three rails 4c, 4d and 4e that are parallel with each other and perpendicular to the two rails 4a and 4b. The rail 4c is placed at the end of the linear rail assembly. The two rails 4c and 4d and a part of the two rails 4a and 4b constitute a frame firmly fixed to the ring 3a in a pivoting manner. The whole of the linear rail 4 can pivot through 360° about the vertical axis of rotation 5 passing through the centre of the ring 3a.

The seat 6b is in sliding engagement with the two rails 4a and 4b. This seat 6b supports in a pivoting manner about the vertical axis of rotation 7 the connecting part 6a which is a metal frame held vertical. The robotic arm 9 is an arm according to the "SERIAL" architecture. It is fixed to an upper part of the connecting part 6a and can pivot about the horizontal axis of rotation 12. The forearm 10 is an elongated tube getting wider at the connection to the connecting part 6a. The free end of the forearm supports the wrist 11 on which is fixed the support table 17 for the patient. This table 17 is kept substantially horizontal for most of the time but it is brought into position by the wrist. The table 17 can be a table or a chair in certain cases for patient transport. It is made of carbon with a honeycomb structure in order to be radio transparent and very rigid whilst having limited weight.

The positioning robot is constituted such that it is compact in its rest position.

For example, a rest position can be the position shown in FIGS. 2 and 3 in which the linear rail 4 and the forearm 10 are practically parallel in the same vertical plane. The connecting part is arranged on one end of the linear rail 4 opposite to the base 3. The forearm 10 is fixed to the connecting part 6a and is directed towards the base 3 whilst remaining parallel with the linear rail 4. The table 17 is kept above the wrist 11, one end being fixed to the wrist 11 and the other free end being on the opposite side from the forearm.

In order to improve its compactness, it is also possible to provide a sliding linear rail such that in the folded position, the overall dimensions are minimal and/or the centre of gravity of the positioning robot is as close as possible to the axis of rotation 5. With a sliding rail, the linear working range, and therefore the working space, is increased.

FIG. 4 is a schematic view of the working space E1 for a positioning robot according to the invention. This space E1 is a volume of hemispherical shape with a flattened top. The patient can thus be positioned continuously in the whole volume of this working space E1.

FIG. 5 shows another embodiment example in which most of the components of the previous example are again present. The connecting part 18 has been modified such that in this embodiment it is possible to install an upper precision connecting part of great weight. In fact, the linear rail 21 is fixed to the floor and can with no problems receive a connecting part 18 which can pivot through 360° about a vertical axis of rotation with respect to a seat 19. This seat 19 slides linearly along a horizontal axis of translation on two parallel linear rails 20 fixed to the floor. For the implementation of this embodiment, a small pit 21 is provided in which are installed the first linear rail 20 and the second rail (not visible in FIG. 5). This positioning robot therefore comprises an axis of horizontal translation on the linear rail and five axes of rotation: rotation of the connecting part 18 with respect to the seat 19, of the forearm 10 with respect to the connecting part, and the three axes of rotation of the wrist 11. Another axis of translation can also be added due to the fact that the forearm 10 can be sliding.

With such a positioning robot, it is possible to guarantee a precise positioning of the tumour to within about ±0.5 mm and about ±0.5 degrees, as well as possibilities of large movements:

Delta X=±1000 mm (longitudinal axis in the nominal version of the linear axis)
Delta Y=±1000 mm (lateral axis)
Delta Z=±800 mm (vertical axis)
Delta Rx=±20 deg (longitudinal axis)
Delta Ry=±20 deg (lateral axis)
Delta Rz=±110 deg (vertical axis)

FIG. 6 shows an example of implementation in which the positioning robot is deployed. The robotic arm is in an upper oblique position. The wrist 11 keeps the table 17 horizontal. It can also be seen that the working space E2 is a volume having the shape of a laterally elongated hemisphere flattened on the top.

FIG. 7 shows another advantageous embodiment of the robot according to the invention. There can be seen a seat 22 which is capable of sliding on two parallel linear rails 23 and 24 arranged laterally with respect to this seat 22. A first motor 25 participates in the linear displacement of the seat 22. A connecting part 26, placed above the seat 22, is connected to this seat 22 in a pivoting manner about a vertical axis. The connecting part has a triangular shape with its base placed on the seat 22 and an inclined flank receiving the robotic arm 9. A second motor 27 participates in the rotation of the connecting part 26 with respect to the seat 22. Advantageously, the robotic arm 9 is connected to the connecting part 26 pivoting about an axis of rotation 28 which is inclined at an angle α which is not zero with respect to the horizontal. This angle α is preferably between 45 and 60°. In the present case, it is 60°. This inclined disposition allows the robot according to the invention to move in a reduced space such as a conventional hospital room with a ceiling limited to 2.5 meters for example, and at the same time reach a minimum height for loading the patient of the order of 60 cm, in particular for a child or an aged person to climb on the table 17. The inclined disposition makes it possible to place the robotic arm 9 and the connecting part 26 on the seat 22 as close as possible to the ground without the rear part 29 of the robotic arm 9 colliding with obstacles, such as the seat itself, during movements of rotation. In fact, in the above embodiments, the robotic arm 9 is fixed to the connecting part at a height sufficient for the rotation of the robotic arm not to intercept the seat 6b, as in FIG. 3 For example.

The robot thus described has six axes of manoeuvrability, one translation and five rotations, that is to say six degrees of freedom. It is therefore possible to place a patient in the working space in any configuration whatsoever.

According to another aspect of the invention also shown in FIG. 7, there can be seen a platform constituted by two half-platforms 30 and 31. The half-platform 30 comprises several slats 32 chain-linked to each other by means of hinges (visible in FIG. 8 at 33). The half-platform 30 is in the unfolded position, i.e. it constitutes a solid flat platform upon which the user can stand. This half-platform 30 slides whilst being integral with the seat 22. Thus, when the seat 22 moves away from a fixed platform on the left 34, the half-platform 30 slides, covering the pit which is between the fixed platform on the left 34 and the motor 25 fixed to the seat 22. On the other hand, when the seat 22 is butted against the fixed platform on the left 34, the half-platform 30 slides in order to assume a folded position, concertinaed under the fixed platform on the left 34. The half-platform 35 acts in the same way as the half-platform 30 but in phase opposition. When one of them is folded, the other one is unfolded, and vice-versa. In FIG. 7, the half-platform 35 is in the folded position under the fixed platform on the right 36. It can be seen that the slats 37 constituting the half-platform 35 are concertinaed under the fixed platform on the right 36.

FIG. 8 shows the sliding mechanism of the half-platform 35 in greater detail, ditto for the half-platform 30. This half-platform 35 slides on two sets of secondary rails.

A first set of inner secondary rails 38 and 39 (shown in dotted line). Each secondary rail 38, 39, comprises an upper linear part 40 (not shown for the secondary rail 38) on which are the slats 37 in the unfolded position allowing the user to walk on them; an S-shaped bend point 41, 42 and a lower linear part 48, 43 parallel with the upper linear part 40 but arranged practically at the bottom of the pit.

A second set of outer secondary rails 44 and 45 are spaced further apart than the inner secondary rails 38, 39. The two outer secondary rails remain linear throughout the displacement of the slats 37. These slats carry at the hinges rollers which are arranged in a staggered manner. Half of the rollers 46 are guided by the two inner secondary rails 38, 39, whilst the other half 47 are guided by the two outer secondary rails 44 and 45, as seen in FIG. 8. More precisely, these rollers are arranged alternately, a roller 46 is followed by a roller 47 and vice versa. In the folded position, the rollers 47 slide in the outer secondary rails 44 and 45, whilst the rollers 46 slide in the bend point 41, 42 which constitutes a ramp accessing a lower level where the lower linear part 43, 48 is located. Thus, in the folded position, the slats 37 are arranged vertically and concertinaed. They then occupy a minimum volume and remain hidden. The slats 37 move from the horizontal state to the vertical state under the effect of gravity alone, and order themselves automatically without additional driving means.

FIG. 9 shows an embodiment of the system according to the invention in a treatment room equipped with the positioning device according to the invention as well as fixed and mobile elements.

The positioning device can be as described previously. Preferably, the positioning device of FIG. 9 is used, comprising a connecting part 50 sliding on a linear rail 56 and carrying a robotic arm 53 provided with a wrist 54 having concurrent axes of rotation.

The linear rail 56 is advantageously fixed to the floor and is constituted by several modular elements 57a . . . , 57d connected to each other. These modular elements can be identical so that their installation in the treatment room is facilitated. With such an arrangement, it is thus easy to produce linear rails of different lengths. As can be seen in FIG. 10, which shows a side view of the positioning device of FIG. 9 without the patient support, each modular element 57a . . . , 57d, comprises an upper plate 67a, 67b, 67c made of metal (or another solid material such as wood, plastic, etc.), placed on three uprights firmly fixed to the floor, two lateral uprights 57h, 57i, and a central upright 57g. Each upper metal plate comprises two slots or lateral openings 58 and 59, as seen in FIG. 9, which are parallel and subdivide each upper metal plate into three parts 67a, 67b, 67c. These slots give access to a confinement volume between the upper metal plates 67b and the floor. This confinement volume houses a motor 66, shown in FIG. 10, intended to make the seat 52 of the connecting part 50 slide with respect to the linear rail 56. More precisely, the seat 52 is borne by runners 68 and 69. These runners comprise an upper part for supporting the seat 52, a lower part sliding on fixed rails 70 in the confinement volume, and a central part designed sufficiently narrow and robust to connect the upper part and the lower part via the slots 58 and 59 without ever touching them.

Such an embodiment makes it possible to hide the motor in a confined volume invisible from the outside, which makes it possible to save space and makes the upper surface of the linear rail flat. The user can move in complete safety over this platform constituted by the upper metal plates of the modular elements 57a . . . , 57d. Two modular stop elements 57e and 57f are also provided, which are respectively arranged at the two ends of the linear rail 56.

The seat 52 is coupled with a pivot part 51 capable of pivoting about a vertical axis of rotation. The robotic arm 53 is connected to an upper part of the connecting part 50 in a pivoting manner about an axis of rotation forming an angle of between 45 and 60° with respect to the horizontal. The wrist 54 carries a patient support 71 which can be positioned very accurately in the frame of reference of the treatment room.

According to the invention, a processing unit 60 makes it possible to control the positioning device or robot electromechanically. Several motors, including the motor 66 for the displacement of the linear rail, are arranged on and in the robot in such a way as to control any articulation of the robot automatically. A set of conventional sensors are arranged on the robot such as for example an inclinometer 65 arranged on the wrist 54. From the sensors as well as in particular from the motors, the processing unit gathers a set of data making it possible to know exactly the positioning of the robot in real time. That is to say that the position of the support in the room and the values of the angles of inclination of the different elements of the robot are known at all times.

The processing unit comprises a hardware part of computer type provided with conventional elements for the acquisition and the analogue and digital processing of data. A hard disk 61 incorporates a 3D display module which determines and then displays on a screen 62 a 3D representation of the displacement of the robot with respect to the environment which is the treatment room. This display module therefore comprises a virtual 3D modelling of the environment and a real-time virtual 3D modelling of the robot moving in the environment. Advantageously, it also comprises a virtual 3D modelling of a virtual envelope around the support 71 of the robot as well as an algorithm for detecting real time collisions between the virtual envelope and the modelled environment.

The modelling of the environment takes account of the dimensions of the treatment room but also of the elements or obstacles present in this treatment room. The processing unit itself as well as a radiation device 64, which is generally mobile, are distinguished in particular. Advantageously, the processing unit is connected to the robot and to the radiation device 64 in a hard-wired 63 or wireless manner, so that the 3D display module can represent any mobile equipment in the treatment room.

The modellings are obtained from data acquired in real time and from predetermined data. These predetermined data can correspond to the positioning data of the mobile elements. These positions, like those of the processing unit, are known in advance and can be entered by the user.

The virtual representation of the dynamics in the treatment room makes it possible to install surveillance systems such as an anti-collision procedure.

In order to do this, provision is made for the virtual envelope to follow the movement of the support 71. FIG. 11 is a virtual 3D representation visible on the screen 62. Only the support 71 is shown for reasons of simplification. The virtual envelope 72 has the same shape as the virtual representation of the support 71 but has bigger dimensions. As a result, when the support 71 is in motion, the envelope 72 follows the same motion and any probable collision of the support 71 with one of the elements of the treatment room is preceded by a virtual collision of the envelope 72 in the 3D display module. In fact, the 3D representation makes it possible to warn the user of the risk of a real collision of the support 71 when the virtual envelope 72 has a virtual collision.

In FIG. 11 the envelope 72 encompasses the 3D representation of the support 71, but this envelope 72 can have a different shape from that of the support and be of smaller size, in particular for monitoring only a part of the support.

The 3D modelling of a virtual envelope can also be used on any mobile element of the treatment room. It is thus possible to provide a second virtual envelope around the radiation device 64, collision being estimated between the two virtual envelopes.

In practice, the display module can be implemented in particular on the basis of 3D driver software and techniques from the field of video games (physical drive) for the calculation of the collisions in an optimum manner. The detection of collisions is based on powerful optimized algorithms such as, in particular, the following algorithms known to a person skilled in the art:

algorithm of the "n-body pruning" type,
temporal coherence algorithm,
distance algorithm of the Gilbert-Johnson-Keerthi type.

These algorithms make it possible to increase the speed of detection of collisions. Approximately 60 collision tests per second can be envisaged.

When a collision is detected, there are several possibilities of action. It is possible to request a complete stoppage of the system or the reorientation of the robot in order to avoid the real collision (for example sliding the robot over a virtual surface).

Such an anti-collision system has numerous advantages:

Persons moving about in the treatment room are kept safe and protected.

The protection system is outside the normal operating system for the hardware in question.

There is an increase in the possibilities of movement, the mobile elements being protected from collision, and therefore an increase in operator convenience with regard to the manoeuvrability of these elements.

An anti-collision system makes it possible to increase the operating capacity of a system that is mobile in space. A medical robot for example is thus easily manoeuvrable by the operator in complete safety without having to worry about a possible contact. The machines are thus more autonomous, and see to their own safety and that of those around them.

According to the invention, provision is made to improve the manipulation of the robot by a co-manipulation process which consists in detecting a force applied to the robot and then in commanding the robot electromechanically in such a way as to favour the movement induced by this force. The applied force generally comes from a user who moves the robot manually by pushing, for example, the patient support using his or her hands.

The co-manipulation process can be an independent process or associated with the anti-collision with virtual envelope technique. In this case, during the manual displacement of the robot during a co-manipulation for example, the processing unit implements collision detection at the same time.

In FIG. 8 for example, the sensor 65a can be a force sensor used to detect any force applied to the wrist 54. This type of force sensor can be constituted by several strain gauges. Several force sensors can be provided distributed over several elements of the robot in order to detect any force applied to this robot.

When it is decided to reorientate the movement of the robot, the anti-collision process allows a slow sliding of the support in the volume of the virtual envelope. This principle makes it possible, in co-manipulation mode, to avoid untimely stoppages of the robot and to smooth the trajectories in the areas around elements present in the treatment room. The sliding is moreover an aid to the manipulation and to the manual guidance of the robot.

Of course, the invention is not limited to the examples which have just been described and numerous adjustments can be made to these examples without exceeding the scope of the invention. In particular it is possible to provide a single central rail upon which the seat can slide.

The invention claimed is:

1. A device for positioning a patient with respect to a radiation, said device comprising:
    at least one horizontal displacement linear rail;
    a seat which is capable of sliding on the linear rail;
    a connecting part capable of carrying out translations with respect to the linear rail and of pivoting about an axis of rotation vertical with respect to that linear rail, said connecting part, being placed above the seat, and connected to said seat in a pivoting manner about a vertical axis of rotation;
    a robotic arm connected to the connecting part, said robotic arm comprising a wrist with concurrent axes of rotation connected to a patient support; and
    said robotic arm is connected to the connecting part in a pivoting manner about an axis of rotation which is inclined with respect to horizontal by an angle $\alpha$ which is not zero between 0° and 90°.

2. The device according to claim 1, wherein the axis of rotation of the robotic arm with respect to the connecting part is inclined with respect to the horizontal by an angle $\alpha$ of between 45 and 60 degrees.

3. The device according claim 1, wherein the linear rail is fixed to a pivoting part of a base, the pivot axis of this pivoting part being vertical.

4. The device according to claim 3, wherein the vertical axis of rotation of the linear rail with respect to the base is merged with an axis of the radiation.

5. The device according to claim 1, wherein the robotic arm comprises a sliding forearm.

6. The device according to claim 1, wherein the wrist is connected to the patient support by an industrial electro-pneumatic tool changer.

7. The device according to claim 1, further including detachable wheels which support the device during installation.

8. The device according to claim 1, further including a mobile platform constituted by two half-platforms connected to the connecting part and arranged on either side of this connecting part in order to constantly cover said at least one linear rail when the connecting part moves;
    each half-platform is constituted by several slats chain-linked to each other by hinges, such that when a half-platform is in a folded position, at least some of the slats of said half-platform are concertinaed under a horizontal plane; said horizontal plane being such that said half-platform, in an unfolded position, is contained in said horizontal plane.

9. The device according to claim 8, wherein the platform slides on two sets of secondary rails:
    a first set of inner secondary rails upon which slides half of the hinges, said two inner secondary rails being parallel and separated from each other; said two inner secondary rails having an upper linear part, a bend point and a lower linear part;
    a second set constituted by two outer secondary rails upon which slides the other half of the hinges, said two outer secondary rails being parallel and separated by a distance greater than the distance separating the two inner secondary rails; said two outer secondary rails being linear in a horizontal plane substantially at a same height as the upper linear part of the inner secondary rails; and in that for two successive hinges, one is borne by the first set of secondary rails, the other being borne by the second set of secondary rails.

10. The device according to claim 9, wherein each half-platform has, in the unfolded position, a flat part close to the connecting part and, in the folded position, a part concertinaed between the lower linear part of the inner secondary rails and the outer secondary rails.

11. The device according to claim 1, wherein the at least one linear rail is constituted by a plurality of modular elements fixed to a floor and connected to each other.

12. The device according to claim 1, further comprising at least one force sensor fixed to the wrist and connected to a processing unit controlling the device for positioning a patient in such a way as to carry out a co-manipulation accompanying any force detected by said at least one force sensor.

13. A positioning system comprising:
    a processing unit integrating supervision software;
    patient resetting sensors;
    a device for positioning a patient with respect to a radiation, comprising:
    at least one horizontal displacement linear rail;
    a seat (22) which is capable of sliding on the linear rail;
    a connecting part capable of carrying out translations with respect to the linear rail and of pivoting about an axis of rotation vertical with respect to that linear rail, this connecting part, being placed above the seat, and connected to said seat in a pivoting manner about a vertical axis of rotation;
    a robotic arm connected to the connecting part, said robotic arm comprising a wrist with concurrent axes of rotation connected to a patient support; and
    said robotic arm is connected to the connecting part in a pivoting manner about an axis of rotation which is inclined with respect to horizontal by an angle $\alpha$ which is not zero between 0° and 90°.

14. The system according to claim 13, wherein the sensors include at least one of the following sensors: an infrared stereovision sensor, X-ray sensors, industrial cameras and a force sensor.

15. The system according to claim 13, wherein the sensors include at least one of the following sensors: a resolver, an accelerometer, an overspeed sensor, an inclinometer, and an anti-collision strip.

16. The system according to claim 13, wherein the processing unit comprises a 3D display module provided with:
    a virtual 3D modelling of a treatment room in which the positioning device is located; and
    a virtual 3D modelling of the positioning device; this modelling being parameterized in order to represent the real-time positioning of the positioning device on the basis of sensors, and to define a virtual envelope around at least one element of the positioning device in order to generate an alarm signal when the virtual envelope collides with a virtual representation of an element of the treatment room.

17. The system according to claim 16, wherein the processing unit is parameterized in order to initiate, in response to the alarm signal, an anti-collision process consisting in stopping of the positioning device or reorientation of the movement of the positioning device.

* * * * *